United States Patent
Ybert et al.

(10) Patent No.: US 11,685,941 B2
(45) Date of Patent: *Jun. 27, 2023

(54) METHOD FOR SYNTHESIZING NUCLEIC ACIDS, IN PARTICULAR LONG NUCLEIC ACIDS, USE OF SAID METHOD AND KIT FOR IMPLEMENTING SAID METHOD

(71) Applicant: DNA Script, Paris (FR)

(72) Inventors: Thomas Ybert, Paris (FR); Sylvain Gariel, Paris (FR)

(73) Assignee: DNA Script, Le Kremlin Bicêtre (FR)

( * ) Notice: Subject to any disclaimer, the term of this patent is extended or adjusted under 35 U.S.C. 154(b) by 155 days.

This patent is subject to a terminal disclaimer.

(21) Appl. No.: 17/070,707

(22) Filed: Oct. 14, 2020

(65) Prior Publication Data

US 2021/0130863 A1 May 6, 2021

Related U.S. Application Data

(63) Continuation of application No. 16/216,857, filed on Dec. 11, 2018, now Pat. No. 10,837,040, which is a continuation of application No. 15/304,701, filed as application No. PCT/FR2015/051022 on Apr. 15, 2015, now Pat. No. 10,913,964.

(30) Foreign Application Priority Data

Apr. 17, 2014 (FR) ........................ 1453455

(51) Int. Cl.
 *C12P 19/34* (2006.01)
 *C12Q 1/6806* (2018.01)
 *C12Q 1/6848* (2018.01)

(52) U.S. Cl.
 CPC ............ *C12P 19/34* (2013.01); *C12Q 1/6806* (2013.01); *C12Q 1/6848* (2013.01)

(58) Field of Classification Search
 CPC ..................... C12Q 2521/113; C12P 19/34
 See application file for complete search history.

(56) References Cited

U.S. PATENT DOCUMENTS

| | | | |
|---|---|---|---|
| 4,772,691 A | 9/1988 | Herman |
| 5,047,524 A | 9/1991 | Andrus |
| 5,262,530 A | 11/1993 | Andrus |
| 5,436,143 A | 7/1995 | Hyman |
| 5,516,664 A | 5/1996 | Hyman |
| 5,602,000 A | 2/1997 | Hyman |
| 5,656,745 A | 8/1997 | Bischofberger |
| 5,744,595 A | 4/1998 | Srivastava |
| 5,763,594 A | 6/1998 | Hiatt |
| 5,798,210 A | 8/1998 | Canard |
| 5,808,045 A | 9/1998 | Hiatt |
| 5,872,244 A | 2/1999 | Hiatt |
| 5,917,031 A | 6/1999 | Miura |
| 5,935,527 A | 8/1999 | Andrus |
| 5,990,300 A | 11/1999 | Hiatt |
| 6,214,987 B1 | 4/2001 | Hiatt |
| 6,232,465 B1 | 5/2001 | Hiatt |
| 6,623,929 B1 | 9/2003 | Densham |
| 6,664,079 B2 | 12/2003 | Ju |
| 6,777,189 B2 | 8/2004 | Wei |
| 7,057,026 B2 | 1/2006 | Barnes |
| 7,078,499 B2 | 7/2006 | Odedra |
| 7,125,671 B2 | 10/2006 | Sood |
| 7,270,951 B1 | 9/2007 | Stemple |
| 7,345,159 B2 | 3/2008 | Ju |
| 7,407,757 B2 | 8/2008 | Brenner |
| 7,544,794 B1 | 6/2009 | Benner |
| 7,566,537 B2 | 7/2009 | Balasubramanian |
| 7,635,578 B2 | 12/2009 | Ju |
| 7,713,698 B2 | 5/2010 | Ju |
| 7,790,869 B2 | 9/2010 | Balasubramanian |
| 7,932,025 B2 | 4/2011 | Carr |
| 7,939,259 B2 | 5/2011 | Kokoris |
| 8,034,923 B1 | 10/2011 | Benner |

(Continued)

FOREIGN PATENT DOCUMENTS

| | | |
|---|---|---|
| EP | 1655381 | 5/2006 |
| EP | 1165786 | 7/2008 |

(Continued)

OTHER PUBLICATIONS

Beabealashvilli et al. (1986) "Nucleoside 5'-triphosphates modified at sugar residues as substrates for calf thymus terminal deoxynucleotidyl transferase and for AMV reverse transcriptase" Biochim. Biophys. Acta., 868(2-3): 136-144.

(Continued)

*Primary Examiner* — Teresa E Strzelecka (74) *Attorney, Agent, or Firm* — Edward J. Baba; Jenny Buchbinder; Bozicevic, Field & Francis LLP (57) ABSTRACT

The invention relates to a method for synthesising long nucleic acids, including at least one cycle of elongating initial fragments of nucleic acids, including a) a phase comprising the enzymatic addition of nucleotides to said fragments, b) a phase comprising the purification of the fragments having a correct sequence, c) an optional phase of enzymatic amplification, each cycle being performed in a reaction medium which is compatible with enzymatic addition and amplification, such as an aqueous medium, the synthesis method also comprising, at the end of all the elongation cycles, a last step of final amplification. The invention also relates to the use of the method for the production of genes, or sequences of synthetic nucleic acids, DNA or RNA. The invention further relates to a kit for implementing said method.

9 Claims, 8 Drawing Sheets

Specification includes a Sequence Listing.

(56) References Cited

U.S. PATENT DOCUMENTS

| | | |
|---|---|---|
| 8,212,020 B2 | 7/2012 | Benner |
| 8,263,335 B2 | 9/2012 | Carr |
| 8,394,586 B2 | 3/2013 | Balasubramanian |
| 8,674,086 B2 | 3/2014 | Liu |
| 8,808,988 B2 | 8/2014 | Zhao |
| 8,808,989 B1 | 8/2014 | Efcavitch |
| 9,121,062 B2 | 9/2015 | Balasubramanian |
| 9,388,463 B2 | 7/2016 | Balasubramanian |
| 9,896,709 B2 | 2/2018 | Makarov |
| 2008/0161548 A1 | 7/2008 | Gupta |
| 2012/0136143 A1 | 5/2012 | Getts |
| 2013/0005612 A1 | 1/2013 | Carr |
| 2014/0363851 A1 | 12/2014 | Efcavitch |
| 2014/0363852 A1 | 12/2014 | Efcavitch |

FOREIGN PATENT DOCUMENTS

| | | |
|---|---|---|
| WO | WO1991/06678 | 5/1991 |
| WO | WO1996/07669 | 3/1996 |
| WO | WO2004/018497 | 3/2004 |
| WO | WO2004/048397 | 6/2004 |
| WO | WO2005/059096 | 6/2005 |
| WO | WO2016/034807 | 3/2016 |

OTHER PUBLICATIONS

Becker et al. (1967) "The enzymatic cleavage of phosphate termini from polynucleotides" J. Biol. Chem., 242(5): 936-950.

Cameron et al. (1977) "3'-phosphatase activity in T4 polynucleotide kinase" Biochemistry, 16(23): 5120-5126.

Canard et al. (1995) "Catalytic editing properties of DNA polymerases" Proc. Natl. Acad. Sci., 92: 10859-10863.

Canard et al. (1994) "DNA polymerase fluorescent substrates with reversible 3'-tags" Gene, 148: 1-6.

Chen et al. (2013) "The history and advances of reversible terminators used in new generations of sequencing technology" Genomics Proteomics Bioinformatics, 11: 34-40.

Ferrero et al. (2000) "Chemoenzymatic transformations in nucleoside chemistry" Monatshefte fur Chemie, 131: 585-616.

Flickinger et al. (1992) "Differential incorporation of biotinylated nucleotides by terminal deoxynucleotidyl transferase" Nucleic Acids Research, 20(9): 2382.

Gebeyehu et al. (1987) "Novel biotinylated nucleotide—analogs for labeling and colorimetric detection of DNA" Nucleic Acids Research, 15(11): 4513-4534.

Guo et al. (2010) "An integrated system for DNA sequencing by synthesis using novel nucleotide analogues" Acc. Chem. Res., 43(4): 551-563.

Guo et al. (2008) "Four-color DNA sequencing with 3'-O-modified nucleotide reversible terminators and chemically cleavable fluorescent dideoxynucleotides" Proc. Natl. Acad. Sci., 105(27): 9145-9150.

IPR2013-00128 re U.S. Pat. No. 7,057,026 Final Written Decision (dated Jul. 25, 2013).

IPR2013-00266 re U.S. Pat. No. 8,158,346 Final Written Decision (dated Oct. 28, 2014).

IPR2017-02172 re U.S. Pat. No. 7,566,537 Decision (dated Apr. 20, 2018).

Ju et al. (2006) "Four-color DNA sequencing by synthesis using cleavable fluorescent nucleotide reversible terminators" Proc. Natl. Acad. Sci., 103(52): 19635-19640.

Knapp et al. (2011) "Fluoride-Cleavable, Fluorescently Labelled Reversible Terminators: Synthesis and Use in Primer Extension" Chem. Eur. J., 17: 2903-2915.

Kobayashi et al. (2004) "A microfluidic device for conducting gas-liquid-solid hydrogenation reactions" Science, 304: 1305-1308.

Kore et al. (2009) "Synthesis and activity of modified cytidine 5'-monophosphate probes for T4 RNA ligase 1" Nucleosides Nucleotides Nucleic Acids, 28(4): 292-302.

Li et al. (2003) "A photocleavable fluorescent nucleotide for DNA sequencing and analysis" Proc. Natl. Acad. Sci., 100(2): 414-419.

Lin et al. (2008) "Recent patents and advances in the next-generation sequencing technologies" Recent Patents in Biomedical Engineering, 2008(1): 60-67.

Michelson et al. (1982) "Characterization of the homopolymer tailing reaction catalyzed by terminal deoxynucleotidyl transferase" J. Biol. Chem., 257(24): 14773-14782.

Motea et al. (2010) "Terminal deoxynucleotidyl transferase: The story of a misguided DNA polymerase" Biochim Biophys Acta, 1804(5): 1151-1166.

Olejnik et al. (1995) "Photocleavable biotin derivatives: A versatile approach for the isolation of biomolecules" Proc. Natl. Acad. Sci., 92: 7590-7594.

Palla et al. (2014) "DNA sequencing by synthesis using 3'-O-azidomethyl nucleotide reversible terminators and surface-enhanced Raman spectroscopic detection" RCS Adv. 4: 49342.

Petrie et al. (1991) "A novel biotinylated adenylate analogue derived from pyrazolo[3,4-d] pyrimidine for labeling DNA probes" Bioconjug. Chem., 2(6): 441-446.

Rasolonjatovo et al. (1999) "Development of a new sequencing method: 3'-ester cleavage catalyzed by Tag DNA polymerase" Nucleosides & Nucleotides, 18(4&5): 1021-1022.

Schmitz et al. (1999) "Solid-phase enzymatic synthesis of oligonucleotides" Organic Lett., 1(11): 1729-1731.

Schott et al. (1984) "Single-step elongation of oligodeoxynucleotides using terminal deoxynucleotidyl transferase" Eur. J. Biochem., 143: 613-620.

Swarup et al. (2014) "Synthesis of new biocarrier-nucleotide systems for cellular delivery in bacterial auxotrophic strains" Tetrahedron, 70(46): 8843-8851.

UD-Dean (2008) "A theoretical model for template-free synthesis of long DNA sequence" Syst. Synth. Biol., 2: 67-73.

Uemura et al. (1989) "Regioselective deprotection of 3', 5' -O-acylated pyrimidine nucleosides by lipase and esterase" Tetrahedron Lett., 30(29): 3819-382.

Written Opinion of the International Searching Authority for PCT/FR2015/051022 dated Sep. 2, 2016.

Wu et al., "3'-O-modified nucleotides as reversible terminators for pyrosequencing" Proc. Natl. Acad. Sci., 104(42): 16462-16467.

Wu et al. (2007) "Molecular engineering of novel nucleotide analogues for DNA seguencing by synthesis" Columbia University, 2008.

Zavgorodny et al. (1991) "1-Alkylthioalkylation of nucleoside hydroxyl functions and its synthetic applications: A new versatile method in nucleoside chemistry" Tetrahedron Lett., 32(51): 7593-7596.

SEQUENCE LISTING

<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: synthetic sequence

```
<400> SEQUENCE: 1
gggggggggg ggggctgcag                                              20

<210> SEQ ID NO 2
<211> LENGTH: 20
<212> TYPE: DNA
<213> ORGANISM: Artificial sequence
<220> FEATURE:
<223> OTHER INFORMATION: synthetic sequence

<400> SEQUENCE: 2
cccccccccc ccccgacgtc                                              20
```

METHOD FOR SYNTHESIZING NUCLEIC ACIDS, IN PARTICULAR LONG NUCLEIC ACIDS, USE OF SAID METHOD AND KIT FOR IMPLEMENTING SAID METHOD

The present invention relates to a process for the synthesis of nucleic acids, in particular of long nucleic acids, and also to a kit for the implementation of this synthesis process.

STATE OF THE ART

Nucleic acid polymers are currently synthesized in vitro by organic synthesis methods. The commonest of these methods is the "phosphoramidite" method described by Adams et al. (1983, *J. Amer. Chem. Soc.*, 105, 661) and Froehler et al. (1983, *Tetrahedron Lett.*, 24, 3171).

This method of synthesis is very widespread and remains the commonest used by the various laboratories and companies having nucleic acid production operations. Due to its degree of use and to the performances which are specific to it, this method constitutes the current reference in terms of synthesis of nucleic acids.

This method employs a coupling reaction between the final nucleotide of a nucleic acid fragment and the nucleotide to be added, the first coupling reaction being carried out between a solid support and the first nucleotide. The coupling is carried out between the 5'-OH group of the final nucleotide of the nucleic acid and the 3'-OH group of the nucleotide to be added. In this way, the synthesis of the nucleic acid is said to be of 3' toward 5' type. During the coupling reaction, the phosphoramidite group is involved in the reaction.

Each nucleotide to be added is protected at the 5'-OH group so as to prevent an uncontrolled polymerization of several nucleotides of the same type, the coupling stage having to result in the addition of just one nucleotide. Generally, the protection of the 5'-OH group is carried out by a trityl group. In order to avoid possible degradation due to the use of powerful reagents, the bases carried by the nucleotides can also be protected. Generally, the protection used involves an isobutyryl group (Reddy et al., 1997, *Nucleosides & Nucleotides*, 16, 1589). After each incorporation of new nucleotides, the 5'-OH group of the final nucleotide of the chain undergoes a deprotection reaction, so as to render it available for the next polymerization stage. The bases carried by the nucleotides making up the nucleic acid for their part are only deprotected after the polymerization is complete.

Between each stage of addition of nucleotide, a specific stage of neutralization is carried out. It consists in permanently modifying the deprotected 5'-OH groups of the fragments which have not incorporated nucleotide in the coupling stage and the sequence of which is in fact incorrect. This stage generally involves an acetylation reaction.

Finally, a last stage of oxidation (for example by treatment with iodine) is necessary to regenerate the phosphodiester bond naturally present between the nucleotides of nucleic acid molecules.

The methods for the organic synthesis of nucleic acids, such as that set out above, require large amounts of unstable, dangerous and expensive reagents which may have an impact on the environment and health. The various stages carried out are also expensive and sometimes difficult to control. Finally, the devices which make it possible to carry out these syntheses in practice are complex, require a major capital cost and have to be operated by a qualified and dedicated workforce.

One of the major disadvantages of these organic synthesis techniques lies in their low yield. During each cycle, the coupling reaction only takes place in 98 to 99.5% of the cases, leaving, in the reaction medium, nucleic acids which do not have a correct sequence. As the synthesis proceeds, the reaction medium thus becomes greatly enriched in fragments comprising a totally incorrect sequence. The errors of deletion type which occur thus have particularly dramatic repercussions resulting in an offsetting of the reading frame of the nucleic acid fragments under consideration.

Thus, for a coupling reaction correct in 99% of the cases, a nucleic acid comprising 70 nucleotides will be synthesized with a yield of less than 50%. This means that, after 70 addition cycles, the reaction medium will comprise more fragments having an erroneous sequence than fragments having a correct sequence. This mixture then proves to be unsuitable for a subsequent use.

Generally, the proportion Z of correct fragments present in the mixture after i addition cycles of nucleotides, each addition having a success rate $\rho$, can be written: $Z=\rho^i$.

Added to the problems brought about by the limit on the effectiveness of coupling are identical problems for all the other reactions involved in the synthesis process. This is because these reactions are not always complete and also promote the creation of nucleic acid fragments comprising an erroneous sequence or a molecular structure not in accordance. These fragments will enlarge the ranks of the impurities as the sequence of the synthesis cycles proceeds.

The methods for the organic synthesis of nucleic acid thus prove to be inefficient for the synthesis of long fragments as they generate a very large amount of fragments having an incorrect sequence, thus regarded as impurities. In practice, the maximum length of the fragments which can be efficiently produced by these methods is between 50 and 100 nucleotides.

There exist alternative techniques using an enzymatic catalyst for carrying out the coupling stage, in particular enzymes which can carry out the coupling reaction between nucleotides in the absence of matrix strand. Several enzymes of polymerase type appear to be suitable for synthesis methods of this type. The enzymes in the category of the polymerases or the ligases capable of creating a phosphodiester bond between two nucleotides, more particularly the enzymes of the family of the telomerases, of the family of the translesion enzymes of polymerase η or ζ type, of the family of the PNPases, of the family of the template-independent RNA polymerases, of the family of the terminal transferases or of the family of the ligases, are included among the enzymes which can act as enzymatic catalysts. The RNA ligase enzyme can be used in this context, and also terminal deoxynucleotidyl transferase (TdT).

These methods of "enzymatic" syntheses make it possible to dispense with the unstable, dangerous and expensive solvents and reagents used during the organic synthesis methods. The enzymatic synthesis methods carry out a polymerization of the nucleic acids in the 5' toward 3' direction. Thus, the coupling is carried out between the 3'-OH group of the final nucleotide and the 5'-OH group of the nucleotide to be added.

In some enzymatic methods, the enzyme which makes possible the polymerization is added directly to natural nucleotides (Deng et al., 1983, *Meth. Enzymol.*, 100, 96). Starting from an initial nucleic acid fragment known as primer, the polymerization enzyme and also the nucleotides of one and the same type are added. The polymerization reaction is then initiated until it is halted by a physical or chemical method. The nucleic acid grows sequentially by repetition of these stages of phosphodiester bond creation.

The use of natural nucleotides results in a phenomenon of uncontrolled polymerization resulting in a very heterogeneous mixture of nucleic acid molecules. This is because nothing prevents the addition of several nucleotides of one and the same type after a first addition. In practice, such a method of synthesis proves to be unusable for the synthesis of nucleic acid fragments having a desired sequence.

The use of protected nucleotides makes it possible to a certain extent to solve this phenomenon of uncontrolled polymerization by completely or partially preventing the creation of additional phosphodiester bonds with respect to that desired, and thus bringing about the halting of the synthesis.

A problem encountered in this case is that of the synthesis of protected nucleotides. The installation of the protection, which can be located on the base or on the 3'-OH group, involves a succession of complex chemical reactions. On conclusion of the synthesis, the nucleotides having the desired protection are rarely present in the pure form. Some impurities, such as unprotected starting nucleotides, very negatively affect the synthesis yields.

Another problem encountered relates to the effectiveness of protection of the nucleotides. According to the strategy selected, the effectiveness of protection is sometimes insufficient to guarantee good synthesis yields. In this case, an effective strategy appears to be the complete prevention of creation of a covalent bond between the terminal nucleotide and a nucleotide present. This generally results in the conversion of the 3'-OH group into another chemical functional group incapable of undergoing a conversion on the part of the enzyme.

Another difficultly relates to the ability to deprotect the nucleotides, once the addition has been carried out, satisfactorily and before the addition planned for the following cycle. Each nucleic acid fragment, the final nucleotide of which fails being deprotected, cannot accept the following nucleotide during the next cycle. This fragment will consequently have an erroneous sequence having the consequence of lowering the yield of the synthesis.

A major problem encountered by enzymatic synthesis methods is the effectiveness of the coupling reaction. Although being greater than that of the organic synthesis methods, the overall coupling effectiveness of the enzymatic methods is well below 100%. Thus, fragments which have failed to add an additional nucleotide remain in the reaction mixture.

This is because the enzyme has to be able to encounter its substrates, a nucleic acid fragment on the one hand and a nucleotide on the other hand, in order to carry out the bonding reaction. As the enzyme and the nucleic acid fragment are macromolecules, their encounter may sometimes not take place within the time allowed. A high concentration of enzyme and of nucleic acid fragments makes it possible to minimize this phenomenon without, however, completely eliminating it. On the other hand, methods involving successive additions of enzyme without a stage of washing or of removal of the excess reagents promote an excessively great dilution of the reagents, resulting in low coupling efficiencies.

Often, the appearance of fragments having an erroneous sequence, which contributes to the fall in the synthesis yield, leads to the addition of a neutralization stage. This stage consists in removing the 3'-OH groups which have not formed a phosphodiester bond. This stage can be carried out by chemical reaction or by the action of an enzyme but it is, in any case, on the one hand, not 100 effective and, on the other hand, it does not remove the fragments concerned, which thus contribute to the heterogeneity of the mixture.

In some processes, after reaction, the enzymes and reagents introduced are inactivated by the addition of other enzymes or reagents or by the application of specific physical conditions. This strategy makes it possible to avoid the washing stages but involves an inexorable increase in the reaction volume with the consequence of a dilution of the reagents and thus a fall in the effectiveness and in the speed of the reactions involved, as described above. In addition, this strategy does not make possible the recycling of some expensive reagents, such as the polymerization enzyme, for example. Finally, this strategy generates a number of consequent reaction wastes resulting from the inactivation of the initial reagents. These wastes, themselves also, contribute to the heterogeneity of the final mixture and to the fall in the synthesis yield by possible inhibitions of enzymes or reagents.

Whatever the methods employed, a large number of impurities accumulate during the synthesis cycles. The impurities predominantly consist of fragments not having the expected sequence of nucleotides. Several strategies are available for removing the fragments of erroneous sequences, such as size exclusion chromatography or polymer gel electrophoresis or fixing to a solid phase. However, the first exhibits performances which are so poor that it cannot be envisaged for the synthesis of fragments of more than about ten nucleotides and the second assumes that the initial nucleic acid fragment is fixed to an insoluble solid support. Thus, in each cycle, simple stages of washing with retention of the solid support make possible the removal of all the impurities, except for the fixed nucleic acid fragments. Although extremely efficient, this strategy does not make possible the removal of the fragments which have not undergone addition of nucleotides during a cycle or those which have been neutralized. Thus, the predominant impurities are not removed, which contributes to the significant fall in the synthesis yield.

Furthermore, the document WO 2005/059096 describes a process for the synthesis of nucleic acids on a solid support followed by the detection and correction of the erroneous sequences. This process requires complex stages of identification or of analysis.

To date, no process for nucleic acid synthesis is truly satisfactory and makes it possible to respond to the problem of synthesis of long fragments, whatever their sequence. One of the foremost reasons is the systematic loss in yield inherent in all the methods proposed to date. In particular, this loss in yield is dependent on the length of the desired nucleic acid and reaches proportions such that it prevents the synthesis of long fragments. Specifically, the direct synthesis of nucleic acid fragments having the size typical of a gene, i.e. between 500 and 5000 nucleotides, is completely inaccessible by the current processes.

A first aim of the invention is to overcome the disadvantages of the methods of the prior art by providing a process for the synthesis of nucleic acids with a high yield.

Another aim of the invention is to provide a process for the synthesis of long nucleic acids, that is to say nucleic acids of at least several hundred or several thousand nucleotides.

Another aim of the invention is to provide a synthesis process comprising a succession of stages which, combined together, make it possible to retain an extremely high synthesis yield, independently of the size of the nucleic acid fragment to be synthesized.

DISCLOSURE OF THE INVENTION

These aims are achieved by the process for the synthesis of nucleic acids according to the present invention, in particular of long nucleic acids, comprising at least one cycle of elongation of nucleic acid fragments, known as initial fragments, comprising n (or of sequence with n) nucleotides, n ranging from 3 to $10^{12}$, each cycle being subdivided in the following way:
a) a phase of enzymatic addition of Xi nucleotides to one end of said fragments, it being possible for X to be between 1 and 5, preferably between 1 and 3, i being the number of the cycle, making it possible to obtain fragments comprising n+Xi nucleotides, known as first phase, and comprising the following stages:
 a first stage of attaching, to a first support, a first end of initial nucleic acid fragments or nucleic acid fragments in the course of elongation, including n nucleotides,
 a stage of addition of the reagents necessary for the enzymatic addition, a stage of enzymatic addition of Xi nucleotides to the second end of said nucleic acid fragments, it being possible for X to be between 1 and 5, preferably 1 and 3, i being the number of the cycle,
 an optional stage of removal of the undesirable reagents from the reaction medium,
 a stage of detaching, from said first support, said fragments comprising n+Xi nucleotides,
 a first stage of transfer of said fragments comprising n+Xi nucleotides,
b) a phase of purification of the fragments having a correct sequence comprising n+Xi nucleotides, known as second phase, comprising the following successive stages:
 a second stage of attaching, to a second support, said fragments comprising n+Xi nucleotides by their end carrying the Xi nucleotides added during the first phase,
 a stage of removal of the fragments which have not been added to and of the fragments which have not been attached to the second support,
 a stage of detaching said fragments comprising n+Xi nucleotides from said second support,
 an optional stage of removal, from the reaction medium, of the undesirable residual reagents;
c) an optional phase of amplification, preferably enzymatic amplification, such as by PCR, of the fragments having a correct sequence comprising n+Xi nucleotides, known as third phase, comprising the following successive stages:
 a stage of addition of the reagents necessary for the amplification,
 a stage (optionally composed of substages making the process possible) of multiplication by a multiplication factor Yi of the fragments comprising n+Xi nucleotides, i being the cycle number, it being possible for Y to be between 1 and $4\times10^{10}$, preferably between 1 and $1\times10^9$,
 a stage of transfer of the fragments comprising n+Xi nucleotides,
each cycle being carried out in a reaction medium compatible with an enzymatic addition and an enzymatic amplification, such as an aqueous medium, the synthesis process also comprising, at the end of all of the i elongation cycles, a stage of final amplification by a multiplication factor Yf.

Each phase of addition by enzymatic catalysis is thus followed by a phase of purification which makes it possible to retain, in the reaction medium, only the fragments of correct sequence comprising n+Xi nucleotides, and these are the only fragments which will be subjected to the optional amplification phase, either between each cycle, or after a predetermined number of cycles, or else solely at the end of the i elongation cycles, when the nucleic acid fragments exhibit the desired length.

The process of the present invention thus makes it possible to synthesize nucleic acid fragments having the desired sequence. It dispenses with the use of model nucleic acid fragments and makes the possible synthesis of products of very high purity, independently of the length and of the nature of the sequence chosen.

More particularly, the phase of purification of the fragments of correct sequence comprising n+Xi nucleotides comprises the removal of the fragments which have not been added to and/or of any other undesirable residual reagent.

The amplification phase is in particular a selective amplification of the fragments having a sequence comprising n+Xi nucleotides, known as correct sequence fragments, multiplying in the reaction medium the fragments having a correct sequence by a multiplying factor more than 10 times greater, preferably more than 100 times greater, than the multiplying factor of the other fragments, known as incorrect sequence fragments, in particular the fragments which have not been added to.

Preferably, the first support exhibits a surface to which are fixed, noncovalently, nucleic acid strands comprising at least three nucleotides, said nucleotides of these strands being complementary to the nucleotides present at the first end of the initial fragments, so as to immobilize, by hydrogen bonds between their respective bases, said first ends of the fragments.

Said first and second supports are advantageously two distinct supports which are provided, for example, in the form of a glass sheet, of a sheet of polymer material or of beads. Preferably, one or other of these supports, advantageously the second support, exhibits magnetic properties.

The first support and the second support advantageously exhibit attaching surfaces of different natures, said first and second supports preferably being distinct, in particular distinct in their spatial location. One of the solid supports can be stationary and the other, for example, mobile in the reaction medium or capable of being displaced.

The synthesis process according to the present invention is based on the use of an enzymatic catalyst to carry out the phosphodiester bonding which makes possible the polymerization of the nucleotides making up the nucleic acid fragments to be produced. More specifically, the process employs, without being limited thereto, enzymes which make possible the creation of the phosphodiester bond between the 3'-OH group of the nucleic acid fragment in the course of synthesis and the 5'-OH group of the nucleotide to be added during the enzymatic addition stage.

In a preferred embodiment, the enzymes used are capable of providing the polymerization of the nucleotides independently of the presence of a matrix model. Such enzymes are then capable of synthesizing nucleic acids in the absence of any one complementary strand in the medium. Furthermore, these enzymes have the ability to synthesize single strand nucleic acid fragments.

The addition of X nucleotides is thus advantageously carried out by the enzymatic route, by means of enzymes capable of polymerizing modified nucleotides without the presence of a matrix strand.

The enzyme is, for example, chosen from the enzymes of the family of the telomerases, of the family of the translesion enzymes, of polymerase q or C type, of the family of the PNPases, of the family of the template-independent RNA polymerases, of the family of the terminal transferases or of the family of the ligases, the template-independent DNA polymerases or else the enzymes of the family of the terminal deoxynucleotidyl transferases (TdT). These enzymes are expressed by certain cells of living organisms and can be extracted from these cells or purified from recombinant cultures.

These enzymes require the existence of an initial nucleic acid fragment known as primer. This initial fragment acts as substrate during the first cycle of elongation of the nucleic acids to be synthesized. It has a 3'-OH group free to react with the 5'-OH group of the first nucleotide to be added.

In a preferred embodiment, the primers have the length most suitable for the implementation of the present invention and also the sequence most favorable to the satisfactory progression of the successive stages. If need be, several different primers can be used simultaneously or successively without limitation of number. This primer can comprise natural nucleotides or modified nucleotides. The nucleotides employed generally consist of a cyclic sugar comprising at least one chemical group at the 5' end and one chemical group at the 3' end and of a natural or modified nitrogenous base.

The conditions of the reaction medium, in particular the temperature, the pressure, the pH, an optional buffered medium, and other reagents, are chosen in order to make possible optimum functioning of the polymerization enzymes while guaranteeing the integrity of the molecular structures of the different reagents also present.

The free end of the nucleotide or nucleotides added to the fragments advantageously comprises a protective chemical group in order to prevent multiple addition of the X nucleotides to one and the same fragment.

The addition of nucleotides protected at their 3' end constitutes one of the preferred embodiments of the present invention, the protective group having the purpose of preventing any possibility of subsequent polymerization, thus limiting the risk of uncontrolled polymerization. In addition to the prevention of the creation of a phosphodiester bond, other functions, such as the interaction with the second solid support or the interaction with other reagents of the reaction medium, can be assigned to said protective group.

For example, the second support can be covered with molecules, such as proteins, making possible a noncovalent bond between these molecules and said protective chemical group, and thus the immobilization, during the second attaching stage, of the fragments which have been added to. The protected nucleotide, and it alone, is capable of interacting with the second solid support. The removal of the fragments which have not been added to can thus be carried out by lack of interaction between their 3' end and the second solid support.

The second phase of the present process does not comprise a stage of detection of the fragments having an erroneous sequence. These fragments are not identified as such and no manipulable information allows them to be identified in order to isolate them or to correct them. The present process simply removes the erroneous fragments by lack of interaction between their 3' end and the second solid support.

The stage of detaching said correct fragments comprising n+Xi nucleotides from said second support can subsequently be carried out by modification of the conditions of the reaction medium, such as modifications to the pH or to the temperature, or under the action of electromagnetic radiation, if said second support is a magnetic support.

Preferably, the first attaching stage corresponds to the attaching of the 5' ends of the starting nucleic acid fragments, or nucleic acid fragments in the course of elongation, to a first support and the second attaching stage corresponds to the attaching of the 3' ends of said fragments comprising n+Xi nucleotides to a second support.

The enzymatic addition is advantageously carried out in the 5' toward 3' direction.

After the purification stage, the deprotection is necessary for the satisfactory progression of the synthesis. Its purpose is to regenerate, at the 3' end, an —OH group capable of reacting during the next polymerization phase and thus to make possible subsequent elongation, during the following i+1 cycle, of the nucleic acid fragments of n+Xi sequence comprising a protected end. The stage of deprotection of said end can in particular employ a chemical reaction, an electromagnetic interaction, an enzymatic reaction and/or a chemical or protein interaction.

Advantageously, the stage of attaching the fragments bonded to the second solid support is concomitant with and inseparable from the stage of deprotection of the protected nucleotides. Conversely, any action which makes it possible to deprotect the nucleotides which have just been incorporated in the fragments in the course of elongation has an irremediable detrimental effect on the abilities of the fragments to interact with the second solid support and consequently results in their detachment.

The present invention advantageously employs an orthogonal mode of synthesis. In this mode of synthesis, certain reagents have properties which allow them not to undergo certain stages, whereas the other reagents will undergo them. More particularly, the synthesis process according to the present invention can be described as "double-orthogonal", that is to say according to two "dimensions": the first dimension relates to the 5' end of the fragments in the course of elongation bonded to a first solid support, and the second dimension relates to the 3' end of said fragments subsequently bonded to a second solid support.

The starting nucleic acid fragment primers thus possess functionalities at their 5' ends allowing them to interact with the first solid support (s) or elements immobilized on these said first supports. The functionalities of the primers are retained throughout the course of the synthesis. The interactions are reversible, in particular by application of specific physicochemical conditions. It is also possible to irreversibly neutralize these interaction characteristics by chemical or enzymatic reaction.

The primers constitute the starting point of the synthesis by receiving the first nucleotide to be added. They are retained throughout this same synthesis up to the addition of the final nucleotide present in the desired sequence. The functionalities present on the 5' end of these primers are advantageously chosen so as to remain functional throughout the synthesis. Consequently, these functionalities confer, on the nucleic acid fragment in the course of elongation, the same characteristics and properties as those initially conferred on the primers, in particular, in the preferred embodiment of the invention, the ability to be attached, during each elongation cycle, to the first solid support, prior to the enzymatic addition stage, via nucleic acid strands already fixed to said first support.

In the preferred embodiment of the invention, the functionalities present at the 5' end of the primers used for the initiation of the synthesis make possible noncovalent interactions with molecules or proteins present on said first solid support. During each stage of the synthesis, these functionalities are retained as they do not react with the reagents employed. The noncovalent bonds are sufficiently strong to provide stable interactions according to certain physicochemical conditions but also sufficiently weak to be eliminated in the event of application of different physicochemical conditions. Finally, the molecular structure of these functionalities can confer on them the possibility of being destroyed or eliminated by the action of specific reagents, it being possible for this property to be of use in the cases where the destruction or elimination of the nucleotides constituting the initial primers is desired.

The surfaces of said solid supports have functionalities allowing them the desired interaction with the functionalities present on the primers. Like the latter, the functionalities of these solid supports have to be able to undergo the different stages of the synthesis cycle without a deterioration in their interaction performances.

The application of certain physicochemical conditions, such as variation in temperature, in pH and/or in electromagnetic field, can make it possible to put an end to the interactions existing between the nucleic acid fragments in the course of synthesis and the solid supports. In other cases, the application of distinct physicochemical conditions from those described above has to make a possible a reinforcing of these interactions. The different physicochemical conditions are applied at the appropriate moments of the cycles of synthesis of the nucleic acid fragments.

More particularly, physicochemical conditions reinforcing the interactions between the first solid support(s) and the 5' ends of the fragments are applied during all the synthesis stages, except during the stages of detachment of the nucleic acid fragments. During these detaching stages, the physicochemical conditions are modified in order to release the fragments.

Between two phases of each elongation cycle, the nucleic acid fragments unfastened from the supports are displaced by creation of a mobile fluid stream, by means of pumps or any other device which makes it possible to displace fluids. More particularly, the fragments are then unfastened from said supports by a liquid stream contributing physicochemical conditions favorable to the nullification of the interaction between the nucleic acid fragments and said supports. The fragments are then displaced while the supports remain immobilized.

The nucleotides which have been added constitute the elementary polymerization entities of the synthesis. They are added one after the other to the nucleic acid fragments. These nucleotides exhibit interaction functionalities in addition to their bonding reactivity functionalities and their protection functionalities. The interaction functionalities of the nucleotides have a similar functioning to the interaction functionalities of the 5' end of the primers.

Preferably, the interaction functionalities of the 5' end of the nucleic acid fragments in the course of synthesis and those of the nucleotides recently added are used jointly during the same synthesis cycle.

The application of specific physicochemical conditions, such as the temperature, the pH, the electromagnetic environment or the presence of filtration material, can be used to carry out the separation between the different supports mentioned above and the nucleic acid fragments of correct or incorrect sequence.

The different stages of the enzymatic synthesis of nucleic acid fragments according to the invention contribute to the performances of this synthesis by providing the correct polymerization of a maximum of nucleic acid fragments and also make possible, via the interaction mechanisms mentioned above, the removal of the largest possible number of nucleic acid fragments not having the desired sequence because they have failed one of the stages constituting the elongation cycle.

Thus, the present invention employs the principle "of wide removal" of nucleic acid fragments. This "wide removal" encompasses predominantly the fragments having an erroneous sequence but also, to a certain extent, fragments having a correct sequence. The purpose of this wide removal concept is to remove all of the fragments having an erroneous sequence, even if this is done to the detriment of the retention of certain fragments having a correct sequence.

Generally, the stages of removal of the impurities, including in some cases the fragments having an erroneous sequence, are carried out by washing operations employing mobile streams of fluids. During the washing stages, the elements which it is appropriate to retain are retained in particular by interaction with the solid supports, for example held immobile or retained by filtration.

Preferably, in the process according to the present invention, the interactions are chosen so as to be selective and thus to act only on nucleic acids with a correct sequence and not on the other compounds present in the reaction medium, such as, for example, the unreacted nucleic acid fragments, the enzymes or components of the buffer solutions. By way of example, the interactions between the nucleotides added and the solid supports are chosen so that only the fragments which have incorporated the protected nucleotides are retained during the washing stages. These same interactions are chosen so as to be sufficiently weak that, in all cases, only the fragments which have incorporated the protected nucleotides are retained during the washing stages. Such weak interactions can have the consequence of not retaining, in a certain proportion, the fragments which have indeed incorporated the nucleotides, even if they had to be retained. This characteristic is desired for the application of the process according to the invention insofar as it provides the completest possible removal of the undesired nucleic acid fragments.

The noncovalent interactions described above are chosen so that they make possible an effective interaction with a proportion of the desired fragments and a zero interaction with the undesired fragments, in particular by optimization of the structure of the entities which interact with one another and optimization of the physicochemical conditions responsible for the interaction. As nonlimiting example, the noncovalent interactions used in the context of the different affinity chromatography or purification techniques make possible such performances.

The synthesis process forming the subject matter of the present invention is also particularly suited to the simultaneous synthesis of nucleic acid fragments. A synthesis cycle making possible the growth of a nucleotide of the desired sequence can be divided into several stages which can be carried out in parallel for the simultaneous synthesis of several different fragments.

Thus, subject to sufficient resources, there is no limitation on the numbers of different nucleic acid fragments which can be synthesized simultaneously. Advantageously, the synthesis in parallel of numerous fragments can significantly increase the capacities for the synthesis of nucleic acids of an experimenter employing the present invention.

In a preferred embodiment of the present invention, in parallel with the synthesis of the desired fragments, it is possible to carry out the simultaneous synthesis of all or a portion of the fragments complementary to those desired.

In another preferred embodiment, syntheses can be carried out simultaneously on fragments having a bond between them. By way of example, the fragments in question can constitute the portions of a larger sequence of interest, such as, but not limited to, a gene, a chromosome region, a chromosome or a genome. Still by way of example, these different fragments constituting a common sequence can have identical or complementary sequence portions facilitating a possible subsequent assembling.

The process according to the present invention includes one or more phases of amplification of the nucleic acid fragments of correct sequence, making it possible to multiply the number of these nucleic acid fragments present in the reaction medium. This nucleic acid chain amplification uses an enzymatic polymerization method combining matrix nucleic acid strands, nucleotides, complementary initial primers and template-dependent polymerization enzymes. The result of the amplification consists of a copy in very large number of the matrix strands initially present. The amplification is carried out by a succession of stages constituting an amplification cycle. The multiplication factor $Y_M$ of the amplified fragments is dependent on the number of amplification cycles m carried out according to the formula: $Y_M = 2^m$.

In a preferred embodiment, the enzymes used for the amplification are capable of providing the polymerization of the nucleotides by copying the matrix strand. Such enzymes are then dependent on a complementary strand. These enzymes have the ability to synthesize double strand nucleic acid fragments.

Examples, nonlimiting for the present invention, of enzymes which can be used for the amplification phase are DNA-dependent DNA polymerases. These enzymes are available commercially and are often purified from recombinant cultures.

The nucleotides employed for the amplification are generally natural nucleotides comprising at least one chemical group at the 5' end of triphosphate type and one chemical group at the 3' end of hydroxyl type and a natural nitrogenous base.

In a preferred embodiment, the nucleotides employed for the amplification are natural nucleotides.

The reaction conditions, such as temperature, pressure, pH, buffer, cofactors and/or other reagents, and also the stages and their sequence, are chosen so as to provide optimum amplification of the fragments under consideration.

The amplification requires the presence of primers complementary to the nucleic acid fragments to be amplified. The complementary primers are short nucleic acid fragments having a nucleotide sequence complementary to that of the fragments to be amplified. For this reason they consist of similar nucleotides which can interact with those constituting the fragments to be amplified. These complementary primers can advantageously be synthesized in parallel to the nucleic acid fragments synthesized according to the process of the present invention. Thus, it is possible, according to this principle, to amplify any sequence under consideration without resorting to any process different from that which is a subject matter of the present invention.

The complementary primers have to interact noncovalently with one of the ends of the fragments to be amplified in order for the amplification enzyme to be able to react. These noncovalent interactions are dependent on and specific to the complementary sequences of the fragments to be amplified and of the primers. Thus, the specificity of these interactions very greatly limits the amplification of the possible fragments not having a correct sequence at their 3' end. In this way, the amplification stage also contributes to the purity of the final result of the synthesis process.

Synthesized Nucleic Acids

The present invention also relates to the nucleic acids synthesized by the process described above. The nucleotide sequence of these nucleic acids can be predetermined, imposing the order of polymerization of said nucleotides during the implementation of the elongation cycles. However, it can be envisaged to use the process of the present invention for the synthesis of nucleic acids having random sequences.

The synthesis process according to the present invention makes possible the synthesis of nucleic acids of all sizes, the minimum size of the nucleic acids nevertheless being determined by the minimum size of the initial primers used during the synthesis. Subject to resources available in sufficient amounts and subject to space and favorable conditions, there is no maximum size of nucleic acids which can be synthesized by the process which is a subject matter of the present invention. In a preferred embodiment of the present invention, it is possible to synthesize nucleic acid fragments having a length of between 3 and $1 \times 10^9$ bases, preferably between 20 and $1 \times 10^7$ bases.

The nucleic acids thus synthesized can comprise nucleotide sequences having multiple biological or biotechnological roles. Advantageously, the present invention replaces a certain number of manipulations of the field of molecular biology and genetic engineering, these tedious and repetitive manipulations normally being carried out by hand by experimenters of the art.

The use of the process of the present invention makes possible a significant increase in the performances and in the productivity of any process employing manipulations of nucleic acids. As nonlimiting examples, the use of the present invention is particularly advantageous in the following fields: preparation of genetic constructs, production of interfering RNA molecules, DNA or RNA chip production, construction of cell strains or lines, enzymatic engineering, development of protein models, development of biotherapies, development of animal or plant models.

The nucleic acids obtained using the process described above can be used directly during manipulations of molecular biology known to a person skilled in the art. The nucleic acids thus obtained exhibit a degree of purity extremely well suited to direct use without the need for additional treatment stages. In an alternative form, the nucleic acids synthesized by the synthesis process according to the invention can undergo additional modifications targeted, for example, at circularizing the nucleic acid fragments, inserting the nucleic acid fragments into expression vectors, inserting the nucleic acid fragments into the genome of living cells, reacting the nucleic acid fragments with other chemical entities or using the nucleic acid fragments for the catalysis of a reaction.

Automation

The automation of the process which is a subject matter of the present invention can be carried out by any preadapted device which can optimize this process, in particular by minimizing the duration of an elongation cycle, by maximizing the accuracy of the additions, washing operations and streams of fluids and by optimizing the reaction conditions employed during the different stages of these cycles.

The process according to the present invention makes possible the synthesis of nucleic acids which can be used directly without additional purification or assembling stages as a result of the high purity of the nucleic acids synthesized, this being independent of their size. The automation of the process which is a subject matter of the present invention for this reason has great industrial and commercial interest.

Kits

The present invention also relates to any kit for the implementation of the process described above, comprising:
- a reaction medium including nucleic acid fragments comprising n nucleotides
- an enzymatic reagent for addition of nucleotides
- nucleotides or combinations of nucleotides capable of being added by said enzymatic addition reagent
- washing and/or buffer solutions for the purification phase
- an amplification reaction medium including: an enzymatic reagent for amplification of nucleic acids, and natural nucleotides capable of being used by the enzymatic amplification reagent
- instructions for use.

Different types of kits can be provided according to the requirements of the experimenter. In particular, different initiation primers can be provided in different kits according to the sequences to be synthesized. Similarly, different types of kits can be provided as a function of an automatic or nonautomatic use.

According to a preferred embodiment, the kit for the implementation of the preferred embodiment of the process of the present invention comprises:
- nucleic acid fragments used as synthesis primer
- a first support for attaching the nucleic acid fragments comprising n nucleotides
- a second support for attaching the nucleic acid fragments which have been added to
- an addition reaction medium including: an enzymatic reagent for addition of nucleotides and nucleotides or combinations of nucleotides capable of being added by the enzymatic addition reagent
- washing and/or buffer solutions for the attaching, purification and detaching stages
- an amplification reaction medium including: an enzymatic reagent for amplification of nucleic acids, and natural nucleotides capable of being used by the enzymatic amplification reagent
- instructions for use.

In addition, the above kit can comprise:
- buffer media favorable to the attaching of the nucleic acid fragments to the first and/or the second attaching support, and/or
- buffer media favorable to the detaching of the nucleic acid fragments from the first and/or second attaching support.

DESCRIPTION OF THE FIGURES

The description of an exemplary embodiment of the preferred form of the invention with use of attaching supports for immobilizing the nucleic acid fragments during certain stages of the synthesis process will be described below with reference to the figures, in which FIGS. 1 to 7 diagrammatically represent the different stages of the process:

FIG. 3 a washing stage and the detaching of the nucleic acid fragments which have been added to;

FIG. 4 the fixing, to a second support, of the nucleic acid fragments which have been added to;

FIG. 5 the deprotection of the nucleic acid fragments which have been added to;

EXAMPLE

With reference to the figures, a cycle of elongation of nucleic acid fragments in the synthesis process according to the invention is described below.

Figure 1:
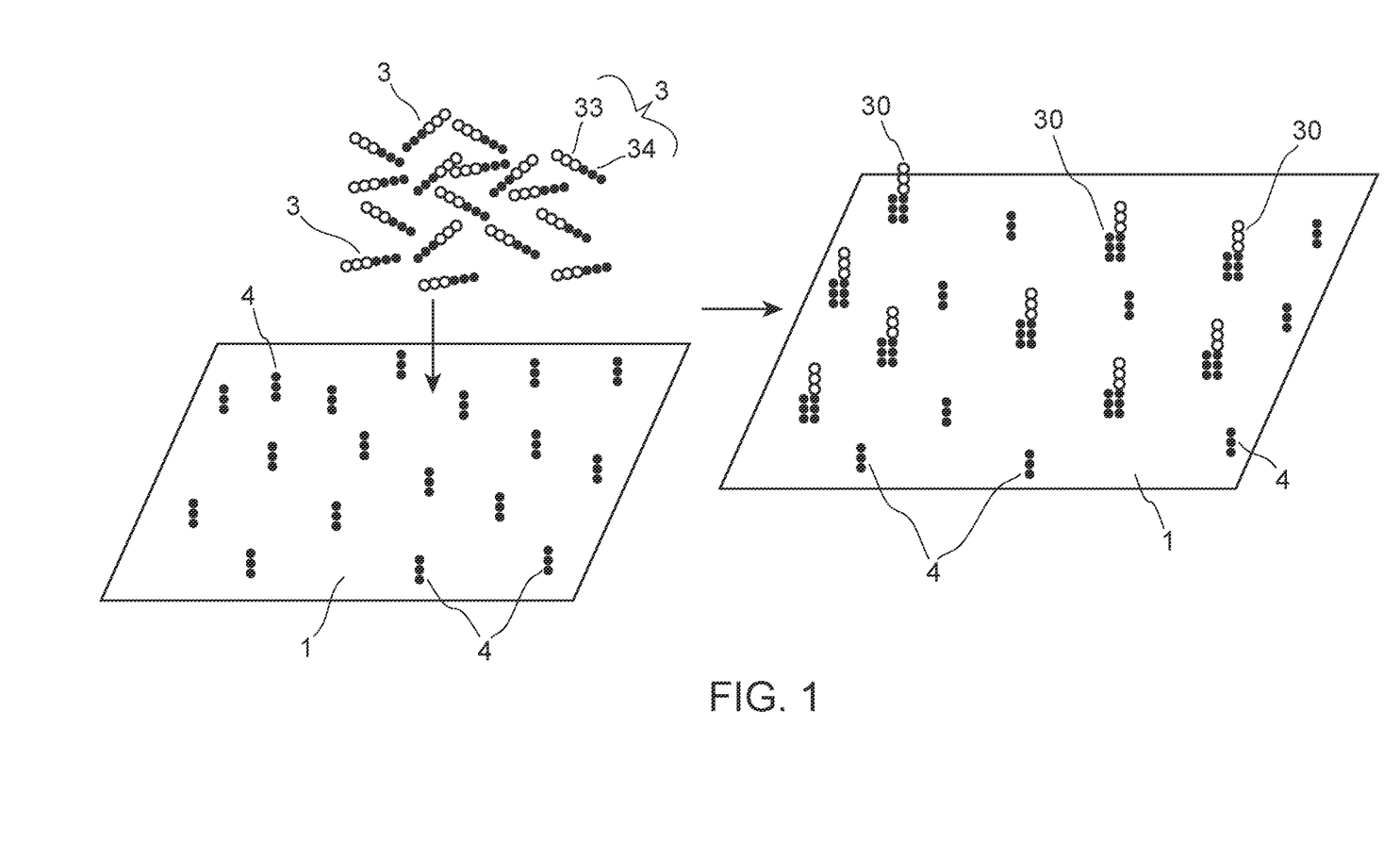
FIG. 1 the immobilization of the starting fragments.

Strands 4 comprising at least three nucleotides are fixed to a first solid support 1, such as a glass sheet. Primers or fragments in the course of elongation 3 of nucleic acids including Xi+n nucleotides are bonded to the strands 4 fixed to the support 1 via hydrogen bonds between their respective bases. The nucleic acid fragment in the course of elongation 3 comprises a free part 33 and an immobilizable part 34 comprising at least three nucleotides complementary to those of the fixed strands 4 and representing the initiator. Nucleic acid fragments 30 immobilized on the first solid support 1 are then obtained in the reaction medium, as represented diagrammatically on the right-hand side of FIG. 1.

Figure 2:
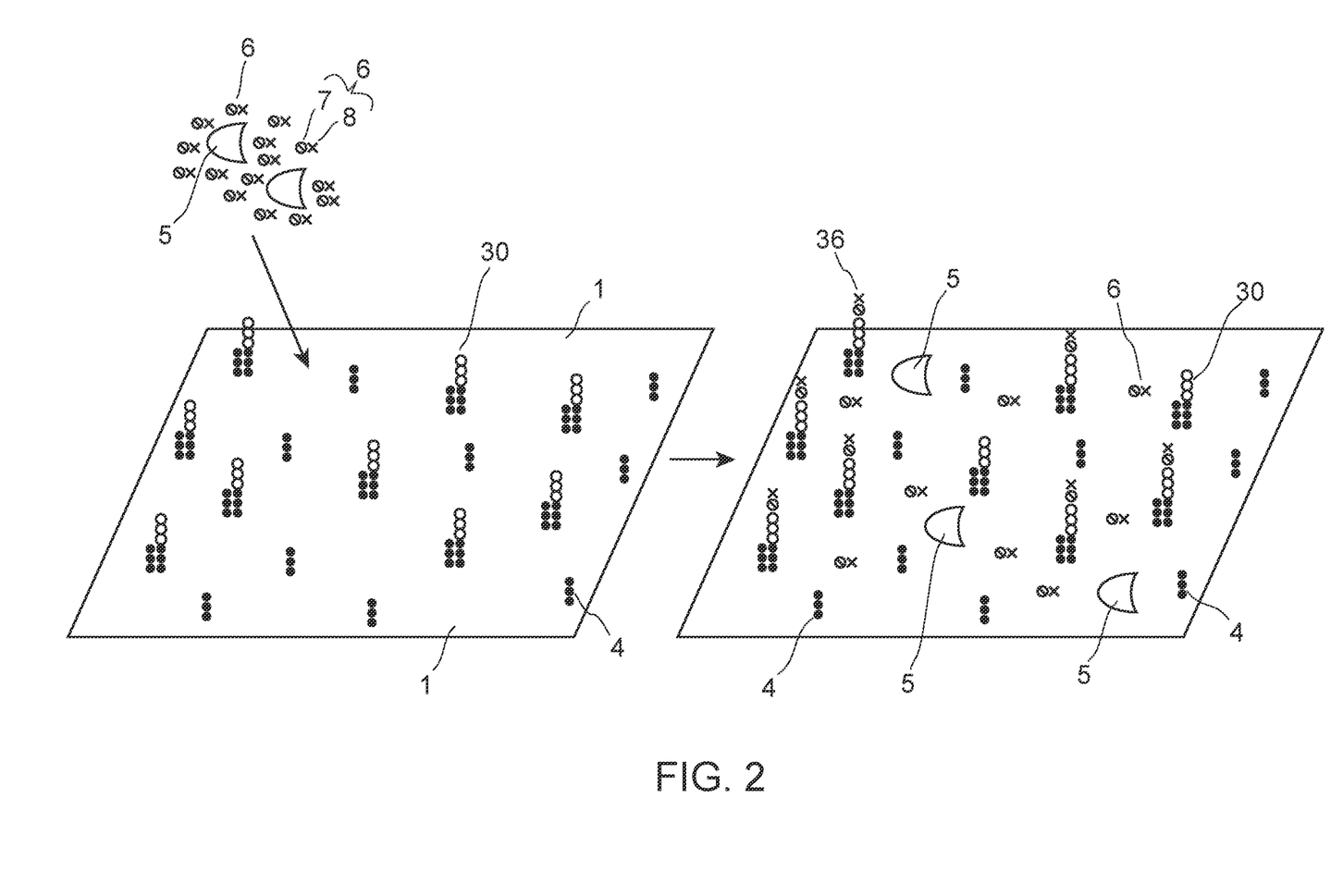
FIG. 2 the addition of a nucleotide to the immobilized fragments.

A stage of enzymatic addition by the addition of a reaction medium including addition enzymes 5 and reagents 6 comprising at least one nucleotide 7, one end of which is blocked by a protective group 8, is subsequently carried out.

This results, as represented diagrammatically on the right-hand part of FIG. 2, in the addition of the reagents 6 to the free end 33 of the fragments 30 immobilized on the first solid support, to give nucleic acid fragments which have been added to (that is to say, having received at least one nucleotide) comprising a protected end, which are immobilized on the support 1. These protected and immobilized nucleic acid fragments are referenced 36.

Figure 3:
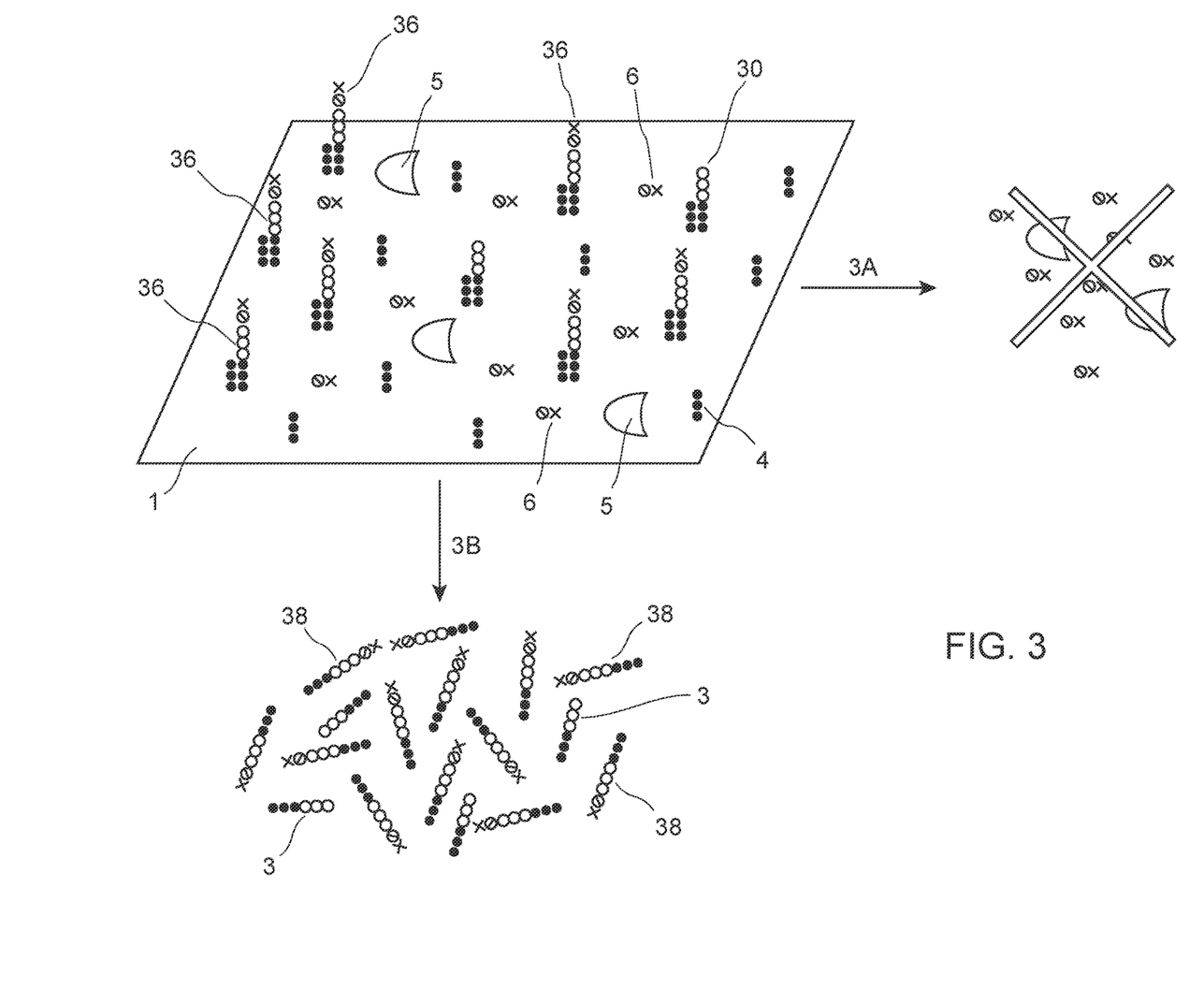

There remain, in the reaction medium, either on the support or close to said support 1, residues of enzymes, reagents 6 and possible buffer solutions, which are then removed by washing according to the arrow 3A. After this first washing operation 3A, the fragments 36 are detached, according to the arrow 3B, from the support 1, which fragments 36 will give free protected fragments which have been added to, referenced 38 in FIG. 3.

However, this detaching stage unfastens, from the support 1, both the fragments which have been added to 38 and the initial fragments 3 which have not been added to. A second support 2, in this instance magnetic beads, covered with a coating 9 formed of proteins, such as antibodies, dihydrofolate reductase (DHFR), avidin, streptavidin, glutathione S-transferase (GST), phosphopeptides (serine, tyrosine or threonine oligomers) or histidine oligomers, then intercedes, as represented diagrammatically in FIG. 4, in the reaction medium including the nucleic acid fragments of correct sequence and the fragments of incorrect sequence.

Figure 4:
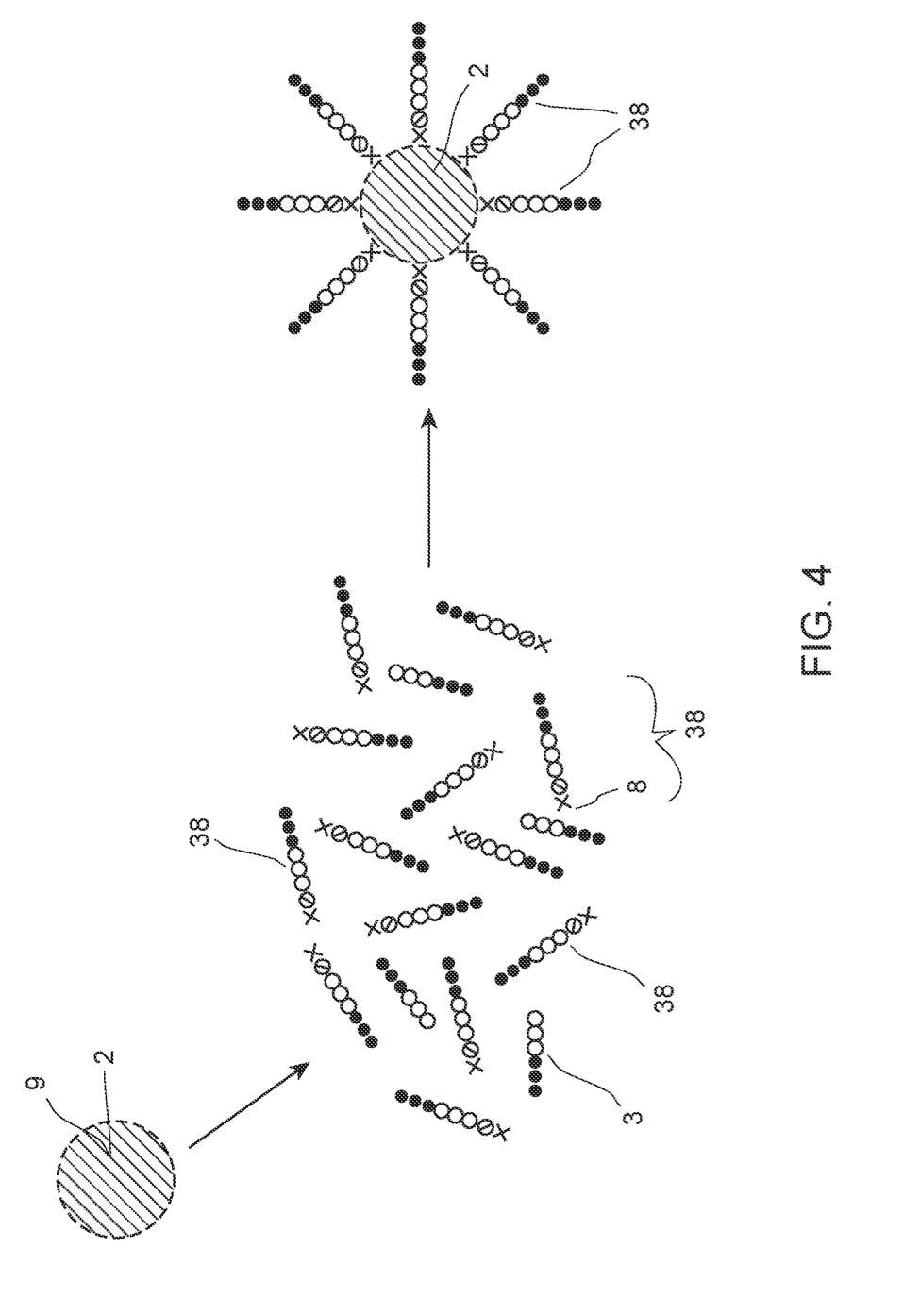

This results in a fixing, by the terminal protective group 8, an attaching, to the surface of the beads 2, of the protected fragments of correct sequence 38. Initial fragments 3 which have not undergone the enzymatic addition and which thus do not comprise an end with the protective group which can become bonded to the proteins of the coating 9 of the beads 2 are then easily removed by washing.

After this stage of effective selection of the fragments which have been added to of correct sequence, the magnetic beads 2 are separated by modifying the conditions of the reaction mixture. For example, modifying the pH, increasing the temperature or the action of a reagent or of an electromagnetic field makes it possible to detach, from the beads 2, the fragments which have been added to in order to obtain free unprotected fragments 37 which have been added to in the reaction medium (see FIG. 5).

Figure 5:
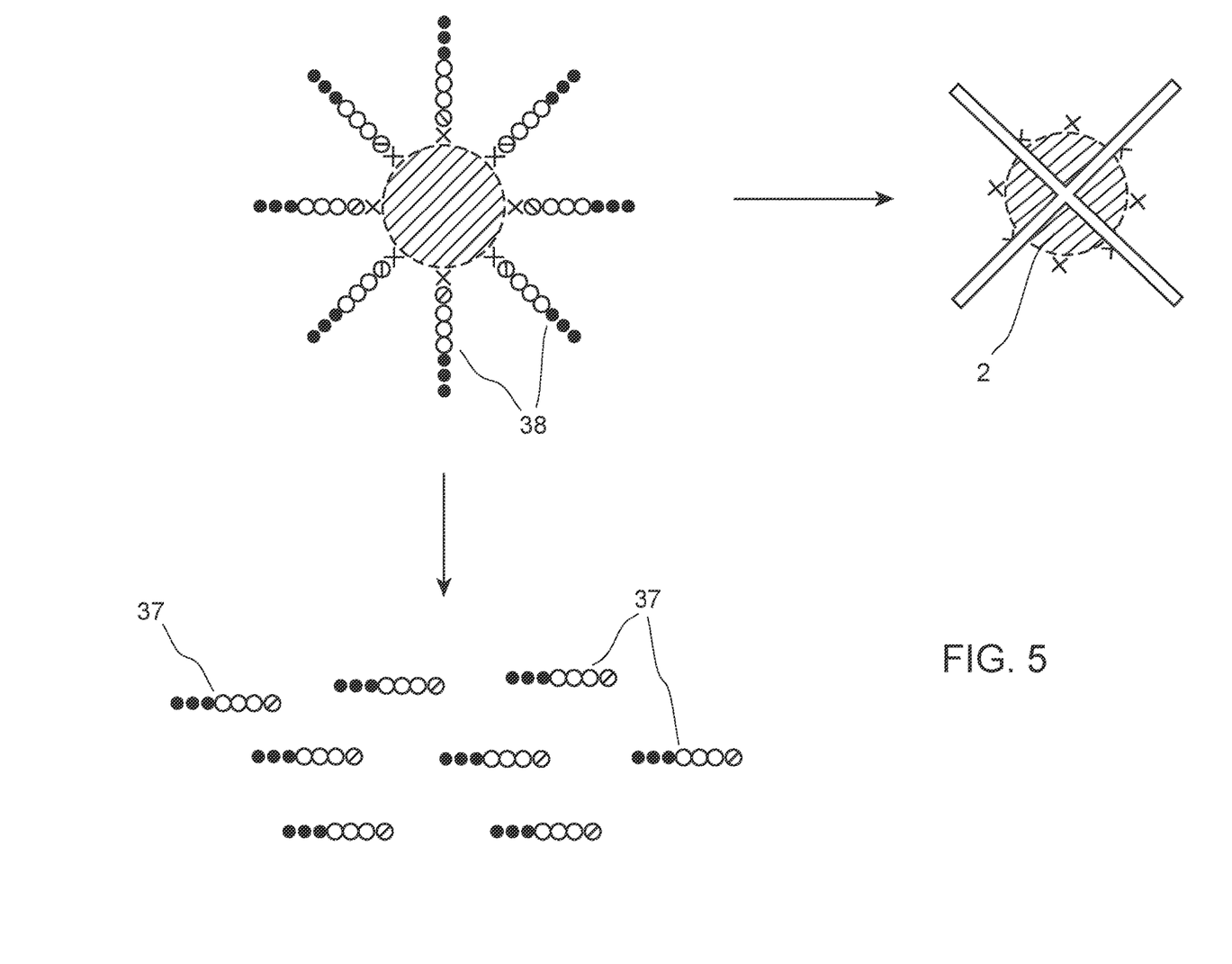

The beads 2 covered with the protective groups which have remained bonded to the coating 9 are then removed from the reaction medium, for example under the action of a magnetic field.

Figure 6:
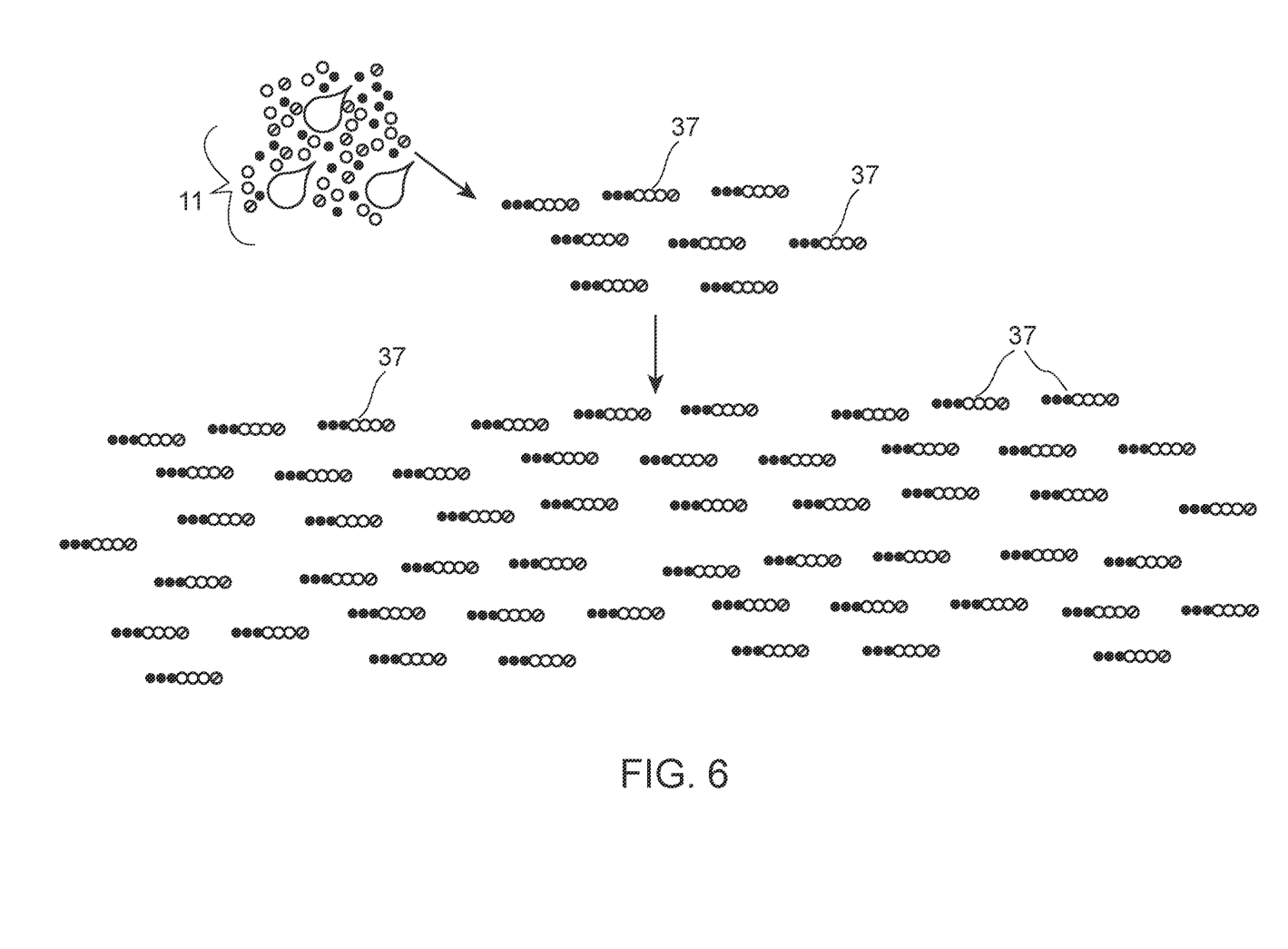
FIG. 6 an amplification stage.

FIG. 6 subsequently diagrammatically represents a stage of amplification of the unprotected fragments 37 which have been added to which have undergone the elongation cycle described up till now, under the action of an amplification reaction medium 11 comprising the amplification enzymes and also the nucleotides, for example the natural nucleotides. The number of nucleic acid fragments 37 is then greatly amplified.

This amplification stage is entirely effective as it amplifies only the fragments 37 which have undergone the elongation cycle. In addition, this minimizes the use of amplification reagents.

No subsequent stage of purification is then necessary, before terminating the synthesis or carrying out a new elongation cycle i+1.

Figure 7:
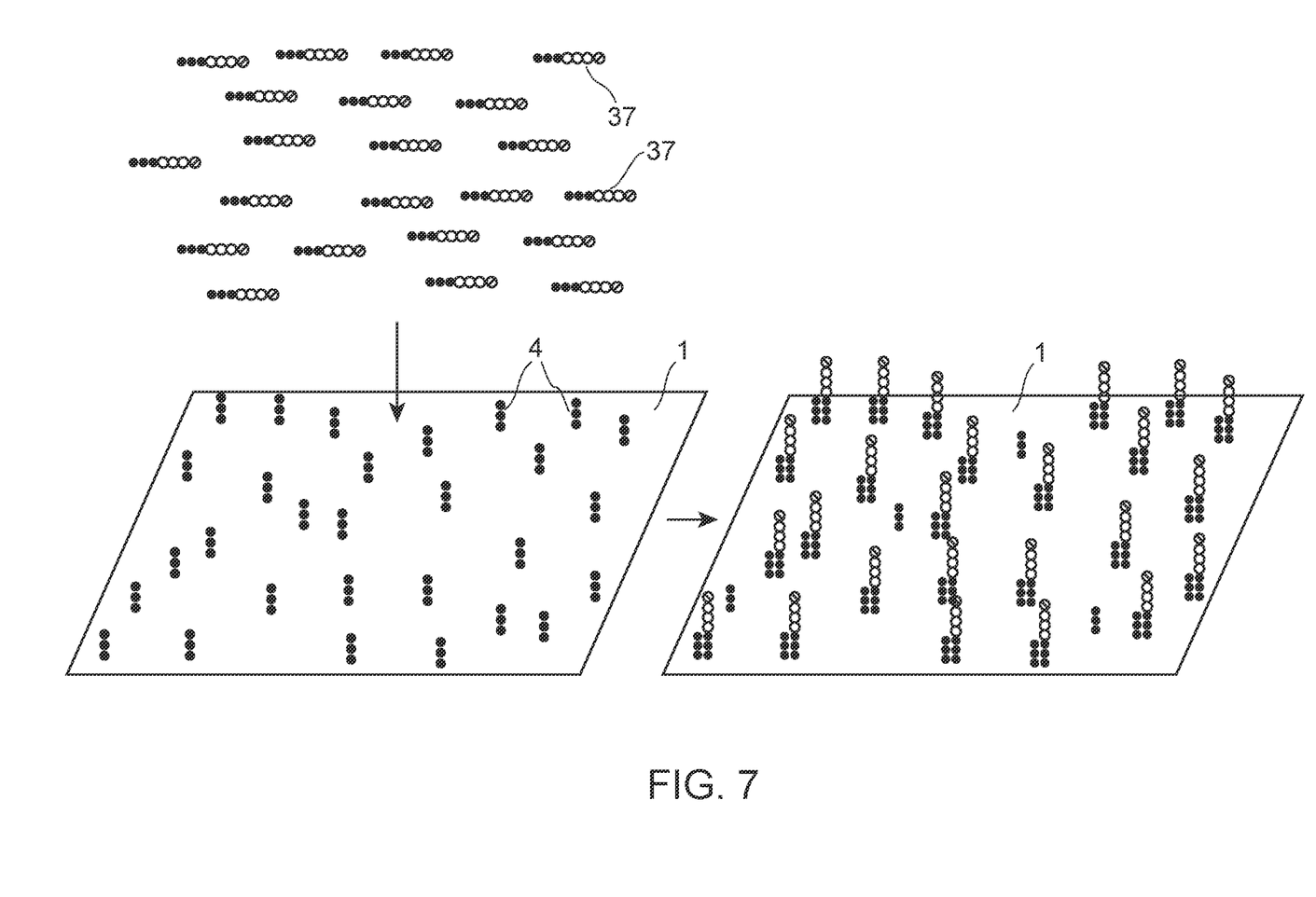
FIG. 7 the initiation of a new cycle using the fragments which have been added to from the preceding cycle.

A new elongation cycle can then occur via the same first solid support 1 to which are fixed the strands 4 used to immobilize the fragments 37, as represented diagrammatically in FIG. 7.

Figure 8:
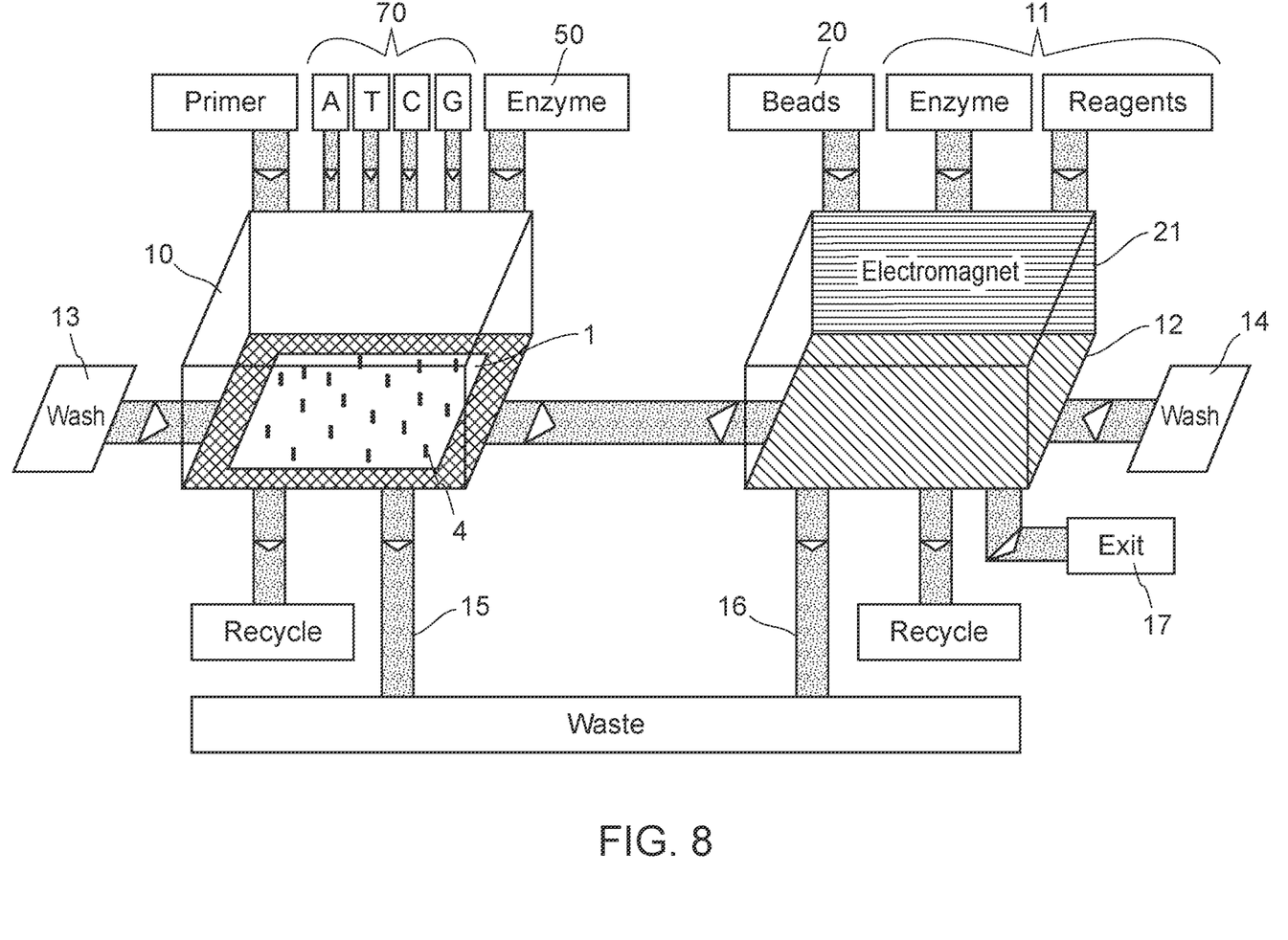
FIG. 8 exhibits a diagram of the possible arrangement of the "reactors" for carrying out the phase of enzymatic addition and the phase of purification of the fragments of correct sequence.

FIG. 8 presents the diagram of an example of an elongation chamber, preferably comprising two separate compartments, in which compartments is carried out each elongation cycle according to the present invention.

The first reactor 10, a compartment in which the enzymatic addition phase is carried out, includes the first solid support 1 to which the strands 4 are fixed and is connected to a device 70 for feeding with addition nucleotides 7 and to a device 50 for feeding with addition enzyme 5.

The second reactor 12, a compartment in which the phase of purification of the fragments of correct synthesis is carried out, is equipped in this instance with an electromagnetic device (electromagnet 21) and is connected to a feed 20 of supports of bead type.

The two reactors 10 and 12, which are separated in order to make possible better purification of the fragments, are nevertheless connected together and connected to inlets 13, 14 for washing solution(s) and also to outlets 15, 16 for wastes to be discharged.

The amplification stage(s) is (are) also carried out within the reactor 12.

The nucleic acids thus synthesized are recovered at the outlet 17 of the second reactor after the final amplification stage.

An example illustrative of the synthesis of a DNA fragment is described below.

The enzyme chosen for carrying out the enzymatic synthesis stages is terminal deoxynucleotidyl transferase or TdT, which is commercially available (Thermo Scientific). It is also possible to produce large amounts of TdT recombinantly.

The primer used to initiate the synthesis is given below:

```
                                    Seq. No. 1
        5'-GGGGGGGGGGGGGGCTGCA*G-3'
```

This primer has a restriction site involving a cleavage of the sequence by the restriction enzyme Pst1 at the arrow present in the above sequence. In the case where the sequence to be synthesized would also comprise a Pst1 site, the initial primer would be modified as required.

The nucleotides used have, at their 5' end, a triphosphate group which promotes their reactivity.

They have one of the four nitrogenous bases naturally present in the DNA molecule, namely A Adenine, T Thymine, C Cytosine or G Guanine, and have, at their 3' end, a group different from the hydroxyl group naturally present and which has the ability to block any subsequent addition of nucleotide by TdT and the ability to interact with other molecules or proteins.

The synthesis conditions used originate from the description of the protocol associated with the enzyme TdT: 50 U of TdT, 200 mM sodium cacodylate, 25 mM Tris-HCl pH 7.2, 8 mM $MgCl_2$, 0.33 mM $ZnSO_4$, 0.2 mM dATP, 2 pmol of primer (Seq No. 1) and 100 μM of protected nucleotides are mixed for a total of 50 μL of reaction volume. The mixture is incubated at 37° C. for 5 min.

Depending on the nature of the protective group chosen, the nucleotides added are deprotected by the action of a mild acid, such as 50 mM sodium acetate pH 5.5, in the presence of 10 mM $MgCl_2$ at 37° C. for 15 min. The deprotection reaction has the result of destroying the bond existing between the nucleotide and the protective group, and also any other group optionally associated with the protective group. According to certain preferred embodiments of the invention, this deprotection stage can simultaneously release the fragment from an interaction at its 3' end.

The DNA fragments in the course of synthesis are incubated at 20° for 10 min in a reaction chamber comprising a glass sheet to which DNA fragments having the following sequence:

```
                                    Seq. No. 2
        3'-CCCCCCCCCCCCCCGACGTC-5'
``` have been fixed beforehand.

The techniques for generating a DNA chip have been employed for the fixing by the 3' end of DNA fragments having the sequence (Seq No. 2). The DNA fragments are thus immobilized in this way.

The washing stages are carried out with a 25 mM Tris-HCl pH 7.2 solution according to a flow rate of 5 μL per second for 30 seconds.

The stages for release of the DNA fragments are carried out by passing a 25 mM Tris-HCl pH 7.2 solution at 95° C. at the flow rate of 5 μL per second for 60 seconds.

The transfers of the free DNA fragments are carried out by means of a system of valves which makes it possible to convey the stream of 25 mM Tris-HCL pH 7.2, in which the fragments are dissolved, into the second rector 12.

The DNA fragments which have undergone the stage of enzymatic elongation using the protected nucleotides are then incubated at ambient temperature for 15 min in the presence of magnetic beads 2 exhibiting, at their surface, a molecule or protein which makes possible the interaction with the final nucleotide added. Magnetic beads coated with GST protein are a nonlimiting example of the type of beads which can be used.

Using a permanent magnet, the magnetic beads 2 carrying the DNA fragments are rendered static while a 25 mM Tris-HCl pH 7.2 stream at a flow rate of 10 μL per second is applied for washing purposes for 30 seconds.

The stage of amplification of the DNA fragments is carried out by the Platinum® Taq DNA Polymerase enzyme (Invitrogen) according to the following protocol: 10× buffer supplied 1×, 0.2 mM dNTP for each nucleotide, 1.5 mM $MgCl_2$, 0.2 μM complementary primer, 1.0 U Polymerase for a total volume of 50 μL.

The amplification cycles used are given by the following table: incubation at 94° C. for 60 sec., application of 30 amplification cycles with the following stages: denaturation at 94° C. for 30 s, then pairing at 55° C. for 30 s, then extension at 72° C. for 60 s per thousand nucleotides to be amplified; a stage of final extension at 72° C. for 5 min is added.

The primer is chosen as a function of the state of progression of the synthesis of the DNA fragments. It has a sequence of approximately 20 nucleotides. The amplification conditions described above are adjusted so as to promote a very specific amplification of the fragments capable of pairing exactly with the complementary primer chosen. The size of this complementary primer is furthermore also chosen as a function of the sequence, so as to promote the most specific amplification possible.

According to the principle disclosed by the present invention, the performances of the different stages were measured and are presented in table 1 below:

TABLE 1

|  | Content of good fragments | Content of bad fragments |
|---|---|---|
| Enzymatic addition | 80% | 20% |
| Purification (Wide removal stages) | 90% | 2% |
| Amplification | 90% | 1% |

The wide removal stages, for example, make it possible to obtain 90% of the fragments having a correct sequence (regarded as "good") and only 2% of the fragments having an incorrect sequence (regarded as "bad").

The repetition of the cycles employing these different stages carefully combined makes possible the synthesis of long fragments, the final purity of which is given by table 2 below (amount of initial primer of 2 pmol):

TABLE 2

| Cycle | Elongation | | Purification | | Amplification | | Purity | |
|---|---|---|---|---|---|---|---|---|
|  | Good | Bad | Good | Bad | Good | Bad | Good | Bad |
| 0 | 9.63E+11 | 2.40E+11 | 8.67E+11 | 4.82E+09 | 8.67E+11 | 4.82E+09 | 99.44% | 0.552% |
| 1 | 6.93E+11 | 1.78E+11 | 6.24E+11 | 3.57E+09 | 6.24E+11 | 3.57E+09 | 99.43% | 0.568% |
| 10 | 3.60E+10 | 9.27E+9 | 3.24E+10 | 1.86E+08 | 3.24E+10 | 1.86E+08 | 99.43% | 0.568% |
| 50 | 70 870 | 18 224 | 63 783 | 365 | 63 783 | 365 | 99.43% | 0.569% |
| 100 | 4 609 640 | 1 185 337 | 4 148 676 | 23 707 | 4 148 676 | 23 707 | 99.43% | 0.568% |
| 500 | 1816 | 467 | 1634 | 10 | 1634 | 10 | 99.392% | 0.608% |
| 1000 | 2852 | 734 | 2566 | 15 | 2566 | 15 | 99.419% | 0.581% |
| 5000 | 94 719 | 24 356 | 85 247 | 488 | 7.67E+13 | 4.88E+09 | 99.994% | 0.006% |

Thus, despite the imperfection inherent in each stage taken separately and despite the presence of fragments failing at various stages of the synthesis, the final result exhibits a purity of more than 99% and can thus be used directly by the experimenter, this being the case independently of the length of the fragment under consideration. The results given by this table are presented as examples and may be substantially different if the parameters (presented in table 1) of content of good and bad fragments generated at each stage, taken as parameters, are different.

INDUSTRIAL APPLICATION

The process which is a subject matter of the present invention makes possible the synthesis of nucleic acids without loss in yield, independently of their length. It makes possible a substantial improvement in the performances of synthesis of nucleic acids with respect to the existing techniques, in particular in terms of simplicity of implementation, of synthesis costs, of synthesis time, of purity of the products obtained and of synthesis capacity. This process can be used for the production of genes or of synthetic sequences of nucleic acids. It is intended in particular for the synthesis of nucleic acids, such as DNA or RNA, for the purposes of research, development or industrial implementation in the field of biotechnology or more generally in the broad field of biology.

The invention claimed is:

1. A method for the synthesis of a nucleic acid sequence, comprising:
   a) attaching initial nucleic acid fragments or elongated fragments to a first support;
   b) contacting the attached initial nucleic acid fragments or elongated fragments with a modified nucleoside triphosphate and a template-independent DNA polymerase so that initial nucleic acid fragments or elongated fragments are elongated by a modified nucleotide, wherein the modified nucleotide comprises a protective group that prevents multiple additions of nucleotides;
   c) deprotecting the elongated fragments;
   d) repeating steps b) and c) until a nucleic acid sequence is obtained;
   e) contacting the elongated fragments with a modified nucleoside triphosphate and a template-independent DNA polymerase so that elongated fragments are elongated by a modified nucleotide, wherein the modified nucleotide comprises a protective group;
   f) detaching the elongated fragments from the first support;
   g) purifying elongated fragments; and
   h) deprotecting the protection groups.

2. The method of claim 1, further comprising amplifying said released elongated fragments.

3. The method of claim 1, wherein said template-independent DNA polymerase is a terminal deoxynucleotidyl transferase.

4. The method of claim 1, wherein said modified nucleoside triphosphate is a 3'-O-protected nucleoside triphosphate.

5. The method of claim 1, wherein said step of purifying comprises specifically binding a 3'-O-protection group to said second support.

6. The method of claim 1, wherein said modified nucleoside triphosphate has a 3'-O-protection group and a protected nitrogenous base.

7. The method of claim 1, wherein said protective group in step e specifically binds to a second support and prevents multiple additions of nucleotides.

8. The method of claim 1, wherein said protective group in step e is a first protective group that specifically binds to a second support and said modified nucleotide further comprises a second protective group that prevents multiple additions of nucleotides.

9. The method of claim 1, wherein said protective group in step e is a first protective group that prevents multiple additions of nucleotides and said modified nucleotide further comprises a second protective group that specifically binds to a second support.

* * * * *

UNITED STATES PATENT AND TRADEMARK OFFICE
CERTIFICATE OF CORRECTION

| | | |
|---|---|---|
| PATENT NO. | : 11,685,941 B2 | Page 1 of 1 |
| APPLICATION NO. | : 17/070707 | |
| DATED | : June 27, 2023 | |
| INVENTOR(S) | : Thomas Ybert et al. | |

It is certified that error appears in the above-identified patent and that said Letters Patent is hereby corrected as shown below:

In the Specification

In Column 1, Line 5, below "METHOD" insert -- Cross-reference to related applications
This application is a continuation of U.S. application Ser. No. 16/216,857, filed Dec. 11, 2018, which application is a continuation of U.S. application Ser. No. 15/304,701, filed Oct. 17, 2016, which application is a 371 of PCT/FR2015/051022, filed Apr. 15, 2015, which application claims priority to French Application Ser. No. 1453455, filed Apr. 17, 2014, the disclosures of which are herein incorporated by reference. --.

In Column 3, Line 34, delete "difficultly" and insert -- difficulty --.

In Column 4, Line 1, delete "100" and insert -- 100% --.

In Column 6, Line 65, delete "q or C" and insert -- η or ζ --.

In Column 8, Line 40, delete "support (s)" and insert -- support(s) --.

Signed and Sealed this
Nineteenth Day of September, 2023

Katherine Kelly Vidal
*Director of the United States Patent and Trademark Office*